US008744867B2

(12) United States Patent
Spertus

(10) Patent No.: US 8,744,867 B2
(45) Date of Patent: Jun. 3, 2014

(54) METHOD FOR SELECTING A CLINICAL TREATMENT PLAN TAILORED TO PATIENT DEFINED HEALTH GOALS

(75) Inventor: John Spertus, Kansas City, MO (US)

(73) Assignee: Health Outcomes Sciences, LLC, Los Angeles, CA (US)

( * ) Notice: Subject to any disclaimer, the term of this patent is extended or adjusted under 35 U.S.C. 154(b) by 1967 days.

(21) Appl. No.: 10/165,855

(22) Filed: Jun. 7, 2002

(65) Prior Publication Data

US 2003/0229513 A1    Dec. 11, 2003

(51) Int. Cl.
*G06Q 30/02* (2012.01)

(52) U.S. Cl.
USPC .................................. 705/2; 705/1.1; 705/3

(58) Field of Classification Search
USPC ................. 705/1–5; 707/1, 10, 100, 200, 205
See application file for complete search history.

(56) References Cited

U.S. PATENT DOCUMENTS

| | | | |
|---|---|---|---|
| 4,839,822 A * | 6/1989 | Dormond et al. ............... | 706/45 |
| 4,846,190 A | 7/1989 | John | |
| 5,517,405 A | 5/1996 | McAndrew et al. | |
| 5,860,917 A | 1/1999 | Comanor et al. | |
| 6,120,460 A | 9/2000 | Abreu | |
| 6,151,581 A * | 11/2000 | Kraftson et al. ................... | 705/3 |
| 6,248,063 B1 * | 6/2001 | Barnhill et al. ................. | 706/21 |
| 6,333,160 B1 | 12/2001 | Tamura | |
| 6,368,272 B1 | 4/2002 | Porumbescu | |
| 6,385,589 B1 | 5/2002 | Trusheim et al. | |

(Continued)

FOREIGN PATENT DOCUMENTS

WO    WO 03/104939 A2    12/2003
WO    WO 03/104939 A3    12/2003

OTHER PUBLICATIONS

Identification of Variables Needed to Risk Adjust Outcomes of Coronary Interventions: Evidence-Based Guidelines for Efficient Data Collection (Peter C. Block, MD, FACC, Eric C. Peterson, MD, MPH,* Ronald Krone, MD, FACC, t Karen Kesler, MS,* Edward Hannan, PHD,:~ Gerald T. O'Connor, PHD, DSc,§ Katherine Detre, MD, FACC, DRPHI[Portland, Oregon.*

(Continued)

*Primary Examiner* — Calvin Loyd Hewitt, II
*Assistant Examiner* — Cristina Owen Sherr
(74) *Attorney, Agent, or Firm* — Knobbe, Martens, Olson & Bear LLP

(57) ABSTRACT

The invention discloses a method by which the health care professional or patient may draw upon historical medical data concerning patients similarly situated in medical condition, to assist him/her in deciding on a clinical intervention procedure to select. This method is specifically tailored to the patient, as data is provided and evaluated from only similarly situated patients, and provides an expectation of potential outcome of the patient should one or the other of the options be selected. The invention further provides a database that may be used in order to provide this comparison based evaluation method. A computer based software system is further disclosed that implements the method. The invention more speiocifically provides a method by which a post-coronary event patient may make an informed decision of which post-coronary revascularization procedure to undergo in the future management of his disease. This method employs the patient's health status date (symptoms, function and quality of life), and provides projections of the patient's expected survival, risk, and 1-year health status outcome from the selection of revascularization procedure, such as Coronary Artery Bypass Grafting (CABG) or Percutaneous Coronary Intervention (PCI).

20 Claims, 10 Drawing Sheets

(56) References Cited

U.S. PATENT DOCUMENTS

| | | | |
|---|---|---|---|
| 6,401,072 B1* | 6/2002 | Haudenschild et al. | 705/3 |
| 6,587,828 B1* | 7/2003 | Sachdeva | 705/1 |
| 7,081,347 B2 | 7/2006 | Yusuf et al. | |
| 7,134,994 B2 | 11/2006 | Alpert et al. | |
| 7,187,992 B2 | 3/2007 | Tuszynski | |
| 8,285,525 B2 | 10/2012 | Soto et al. | |
| 2002/0049615 A1* | 4/2002 | Huber | 705/3 |
| 2002/0165855 A1 | 11/2002 | Ohtomo | |
| 2003/0233250 A1* | 12/2003 | Joffe et al. | 705/2 |
| 2004/0002873 A1* | 1/2004 | Sachdeva | 705/2 |
| 2004/0172291 A1 | 9/2004 | Knowlton | |
| 2005/0131738 A1* | 6/2005 | Morris | 705/2 |
| 2005/0203773 A1 | 9/2005 | Soto et al. | |
| 2006/0200549 A1 | 9/2006 | Soto et al. | |

OTHER PUBLICATIONS

Identification of Variables Needed to Risk Adjust Outcomes of Coronary Interventions: Evidence-Based Guidelines for Efficient Data Collection (Peter C. Block, MD, FACC, Eric C. Peterson, MD, MPH,* Ronald Krone, MD, FACC, t Karen Kesler, MS,Edward Hannan, PHD,:~Gerald T. O'Connor, PHD, DSc,Katherine Detre, MD, FACC, DRPH; JACC vol. 32, No. 1, Jul. 1998.*

John Spertus, et. al.; Health Status Predicts Long-Term Outcome in Outpatients with Coronary Disease; Circulation—Journal of the American Heart Association; Jul. 2, 2002; pp. 43-49.

Colleen A. McHorney, et. al.; The MOS 36-Item Short-Form Health Survey (SF-36): II. Psychometric and Clinical Tests of Validity in Measuring Physical and Mental Health Constructs; Medical Care; 1993; pp. 247-263; vol. 31-No. 3; J.B. Lippincott Company.

T A Rockall, et al; Risk Assessment After Acute Upper Gastrointestinal Haemorrhage; Gut; 1996; pp. 316-321; vol. 38.

Ga L'Abbate, et al.; On-Line Integration and Analysis of Cardiological Data to Support Medical Decision Making; IEEE; Computers in Cardiology; 2004; pp. 189-192; vol. 31.

Elizabeth R. Delong, et al.; Comparing the Areas Under Two or More Correlated Receiver Operating Characteristic Curves: A Nonparametric Approach; Biometrics; Sep. 1988; pp. 837-845; vol. 44.

William A. Knaus, et al.; Apache II: A Severity of Disease Classification System; Critical Care Medicine; Oct. 1985; pp. 818-829; vol. 13-No. 10; The Williams and Wilkins Co.

Frederic D. Wolinsky, et al.; Perceived Health Status and Morality Among Older Men and Women; Journal of Gerontology; 1992; pp. S304-S312; vol. 47-No. 6.

Philip S. Wells, et al.; Accuracy of Clinical Assessment of Deep-Vein Thrombosis; The Lancet; May 27, 1995; pp. 1326-1330; vol. 345.

Salim Yusuf, et al.; Effect of Coronary Artery Bypass Graft Surgery on Survival; Overview of 10-year results from Randomised Trials by the Coronary Artery Bypass Graft Surgery Trialists Collaboration; The Lancet; Aug. 27, 1997; pp. 563-570; vol. 344.

Peter C. Block, et al.; Identification of Variables Needed to Risk Adjust Outcomes of Coronary Interventions: Evidence-Based Guidelines for Efficient Data Collection; JACC; Jul. 1998; pp. 275-282; vol. 32-No. 1; Elsevier Science Inc.

Robert H. Jones, et al.; Identification of Preoperative Variables Needed for Rish Adjustment of Short-Term Morality after Coronary Artery Disease; JACC; Jan. 1988; pp. 20-26; vol. 281-No. 14.

Robert M. Califf, et al.; Importance of Clinical Measures of Ischemia on the Prognosis of Patients with Documents Coronary Artery Disease; JACC; Jan. 1988; pp. 20-26; vol. 11-No. 1; Elsevier Science Inc.

John S. Rumsfield, et al.; Health-Related Quality of Life as a Predictor of Mortality Following Coronary Artery Bypass Graft Surgery; JAMA; Apr. 14, 1999; pp. 1298-1303; vol. 281-No. 14.

Susan Gross Fisher, et al.; Mortality Ascertainment in the Veteran Population; Alternatives to the National Death Index; American Journal of Epidemiology; 1995; vol. 141-No. 3; The Johns Hopkins University School of Hygiene and Public Health.

John Spertus, et al; Association Between Depression and Worse Disease-Specific Functional Status in Outpatient with Coronary Artery Disease; American Heart Journal; Jul. 2000; pp. 105-110; vol. 140-No. 1.

John Spertus, et al.; Monitoring the Quality of Life in Patients with Coronary Artery Disease; The American Journal of Cardiology; Dec. 15, 1994; 1240-1244; vol. 74.

John A. Spertus, et al.; Development and Evaluation of the Seattle Angina Questionnaire: A New Functional Status Measure for Coronary Artery Disease; JACC; Feb. 1995; pp. 33-341; vol. 25-No. 2; American College of Cardiology.

Ge Soto, et al; PRISM. A Web-Based Framework for Deploying Predictive Clinical Models; Computers in Cardiology; Nov. 2004; pp. 193-196; vol. 31; IEEE.

Eric L. Eisenstein, et al.; Assessing the Clinical and Economic Burden of Coronary Artery Disease; 1986-1998; Medical Care; Nov. 8, 2001; pp. 824-835; vol. 39-No. 8; Lippincott Williams & Wilkins, Inc.

William Cassidy; http://archive.gamespy.com/halloffame/september02/pcs/; Pinball Construction.Set; Bill Budge and Electronic Arts; 4 sheets.

Gabriel E. Soto, et al.; Prism: A Novel Tool for Deploying Predictive Clinical Models; Circulation; May 25, 2004; p. 47; vol. 109-No. 20.

Rabin, D. S.; Qadeer; U.; Steir, V.E. "A Cost and Outcome Model of Fertility Treatment in a Managed Care Environment." Fertility & Sterility 1996, 66, 896-903.

Hu, Charles et al.; http://www.medcacl.com/heartrisk.html; Coronary Heart Disease Risk Calculator; Jan. 15, 2000; 1 sheet.

Visiontree; various pages from http://www.idegomethodologies.com; 2004; Idego Methodologies; 19 sheets.

Soto, Gabrielle E. et al.; PRISM Update: Experiences Using a Web-based Framework for the Depolyment of Predictive Clinical Models at the Point of Care; Poster Presentations e341.

"Virtual Offices Basic Manual for Professional" by Help Horizons.com v1.14, Apr. 2001, 60 pages.

* cited by examiner

METHOD FOR SELECTING A CLINICAL TREATMENT PLAN TAILORED TO PATIENT DEFINED HEALTH GOALS

FIELD OF THE INVENTION

The present invention lies in the field of clinical treatment plan assessment and selection, as a method for selecting the particular regimen best suited for a particular patient's individual health goals and desired outcomes is disclosed. The invention also relates to the field of computer software programs, as the method for clinical treatment assessment and selection may be implemented through the use of a computer program and associated software program. The invention further relates to the field of cardiac patient care, as the described method of assessment and treatment selection is particularly defined in some aspects for use in the treatment of a patient that has cardiac disease, such as coronary artery disease.

BACKGROUND OF THE INVENTION

Statement of the Problem

Patient-reported health status has been used as been used as an endpoint in clinical trials. Health status measures quantify the patient's perception of how a disease affects them. Specifically, these developed parameters have been created to allow the patient to report on a subjective level how their disease has affected their everyday function, disease or other symptoms, and generally their perceived quality of life. Apart from being reported as an endpoint, the information obtained from patients on these factors has not been examined or proposed for any other use.

Cardiovascular disease continues to be common in a large percentage of the population, despite improvements made in general in towards improvement in life-style to enhance heart heath. The patient with coronary artery disease, for example, after a cardiac event such as a heart attack, is and the heathcare professional are then faced with selecting a post-cardiac event treatment regimen or clinical intervention procedure, such as Coronary Artery Bypass grafting (CABG) or Percutaneous Coronary Intervention (PCI). Post-cardiac event treatment decisions are presented for the most part in a vacuum to the patient, as no statistical data or factually based decision tree criteria that can be of a full range of clinical outcomes including health status has to this been available against which the patient may make an informed and conscious decision Current clinical evidence collected from patients having had one of two revascularization procedures have shown no difference in the patient survival data. However, survival data is only one criterion in examining and evaluating a selected revasulariztion procedure. Improving a patients' health status outcomes (symptoms, function, and quality of life) is an important critical goal of treament selection, yet essentially no data about the health status outcomes after revascularization exists. With limited outcomes data to differentiate between the relative risks and benefits of CABG and PCI, for example, selecting a mode of coronary revascularization is currently determined almost exclusively by technical considerations and procedural risks. These factors in essence exclude patient participation in the decision making process.

A need continues to exist in the medical arts of a method that may be used that would allow both the patient and the attending health care professional to make a clinical health care treatment decision that would optimize the patient's desired heath goals and quality of life concerns. Such a method would incorporate the patient's individual age, sex, socioeconomic, demographic and clinical characteristics, and provide a patient-tailored set of options with the associated relative risk and success outcomes that are likely to be expected. Such a method des not currently exist in the art.

SUMMARY OF THE INVENTION

The invention in a general and overall sense provides a method for preparing a disease-specific database for use in assessing health care options available to a patient.

In some embodiments, the methods of the invention are employed in the evaluation and decision making process for treatment plan in post-cardiac event patients. Currently, no such method for the post-coronary event patient is described or available.

The database described as part of the present invention may in another aspect provide a method by which the post-coronary or other clinical patient, or his attending health care professional, may create a decision matrix that can be used to consider and select the most appropriate revascularization or other post-coronary event intervention procedure for the patient. This provides the patient with a set of options that is specifically tailored for that patient, and provides the patient with an assessment of the relative benefits and disadvantages associated with selecting one or another of the options being presented.

In another aspect, the invention provides a computer based software system that is devised so as to indicate relative risk associated with the selection of a particular revascularization protocol, given the specific health status of a given patient considering potential options for the treatment of their coronary disease.

BRIEF DESCRIPTION OF THE DRAWINGS

FIG. 1A is a graph of angina frequency post-PCI (Percutaneous Coronary Intervention) (diamond is econonomically burdened patient; square is not economically burdened patient). Patients characterized as not economically burdened demonstrate a higher frequency of angina after PCI revascularization procedure. FIG. 1B is a graph of angina frequency in patients post-CABG revascularization. Patients characterized as economically burdened had about the same frequency of angina post CABG as did the patient population characterized as economically burdened.

FIG. 2B is a graph demonstrating the frequency of angina in a post-coronary event patient that had an angioplasty. The same complications were monitored in these patients, with a reported frequency of 0.1% death, 0.02% stroke, 30% readmission to the hospital, and 20% Re PTCA.

DETAILED DESCRIPTION OF THE INVENTION

Figure 3:
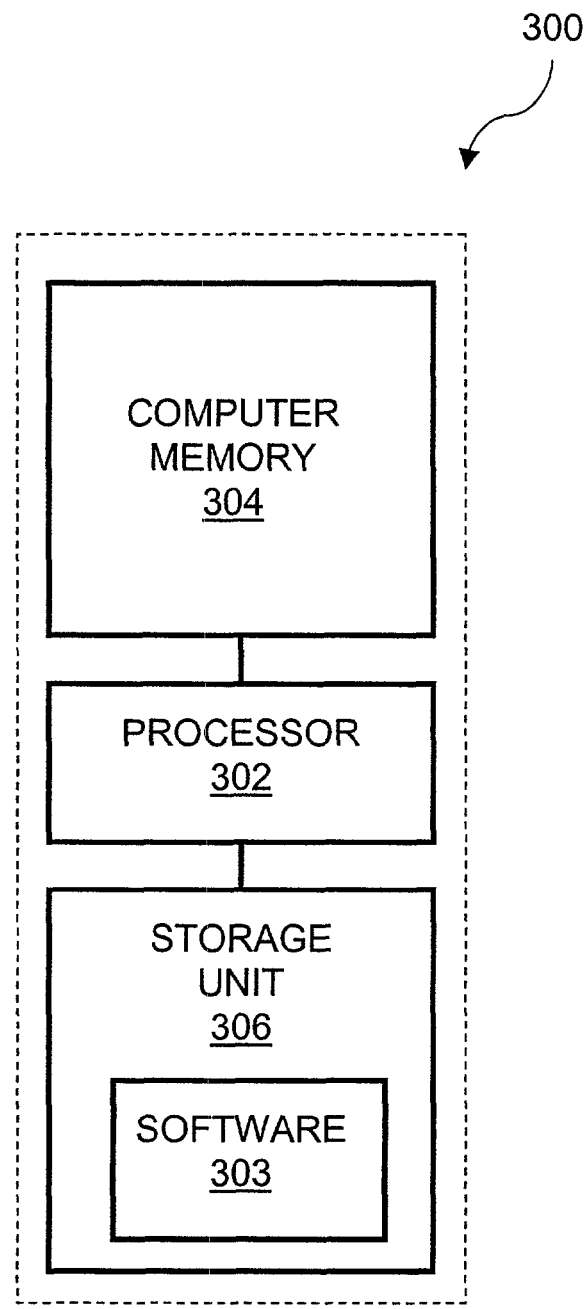
FIG. 3 block diagram illustrating a computer system according to one embodiment of the present invention.

FIG. 3 shows computer system 300 configured adapted for use in a medical or clinical health care facility to identify an appropriate post-cardiac event regimen for an individual patient considering options for post-coronary event treatment, in accord with one embodiment of the invention. Computer system 300 may include processor 302, computer memory 304, and storage unit 306. In computer system 300, processor 302 is communicatively connected to computer memory 304 and to storage unit 306 for operating in accord with the invention. In one embodiment, computer system 300 is configured for identifying a disease state and demographics of the individual patient. Computer system 300 may assess health status parameters from the individual patient to provide a first data assessment profile and identify the projected health outcome desired by the individual patient based upon said individual preferences and goals. Computer system 300 may assess health status parameters from a population of patients having similar demographics to said individual patient, said population of patients having received different treatments, thereby providing a library of specific projected health outcomes for each different treatment. Upon assessing the health status parameters from the population of patients, Computer system 300 may select preferred outcomes from the library of specific projected health outcomes that similarly coincide with preferences and goals of the individual patient, present the preferred outcomes to the patient, and select a clinical treatment for the patient based on the preferred outcomes. In one embodiment of the invention, software 303 is configured for operatively controlling computer system 300 and may initially reside in storage unit 306. Upon initializing computer system 300, software 303 may be loaded in computer memory 304. Processor 302 may then software run 303.

Figure 4:
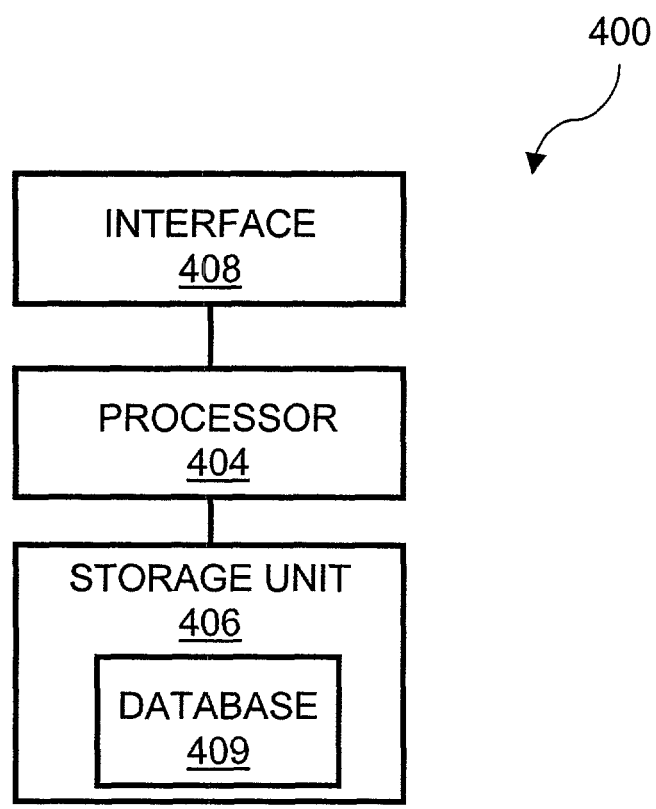
FIG. 4 is a medical system according to one embodiment of the present invention.

FIG. 4 shows medical system 400 configured for configured identifying an appropriate post-cardiac event regimen for an individual patient considering options for post-coronary event treatment, in accord with one embodiment of the invention. Medical system 400 may include processor 404, storage unit 406, and interface 408. In medical system 400, storage unit 406 is configured for configured for storing group data in a database. The group data may comprise responses to a questionnaire having a plurality of questions regarding quality of life and demographic information. The response may be derived from a plurality of patients having survived a coronary event. A first group of the patients have received a post-coronary event revascularization procedure. A second group of the patients had not received the post-coronary event revascularization procedure. Demographics of the first and second groups of patients may be similar to those of the individual patient. In medical system 400, interface 408 is configured for receiving responses to the questions from the individual patient. In medical system 400, processor 404 is communicatively connected to interface 408 and to storage unit 306 for performing statistical analysis on the responses from the plurality of patients and from the individual patient. A comparison of the statistical analysis of the responses from the group of patients and from the individual patient may provide a basis upon which the individual patient may select a post-cardiac event treatment appropriate to preferences and goals of the individual patient.

With further regard to FIGS. 3 and 4, those skilled in the art should appreciate that storage unit 406 and storage unit 306 may illustratively represent the same storage memory and/or one or a combination of storage unit 306 and computer memory 304 within computer system 300. Processor 302 may incorporate functionality including processor 404, for example.

Figure 5:
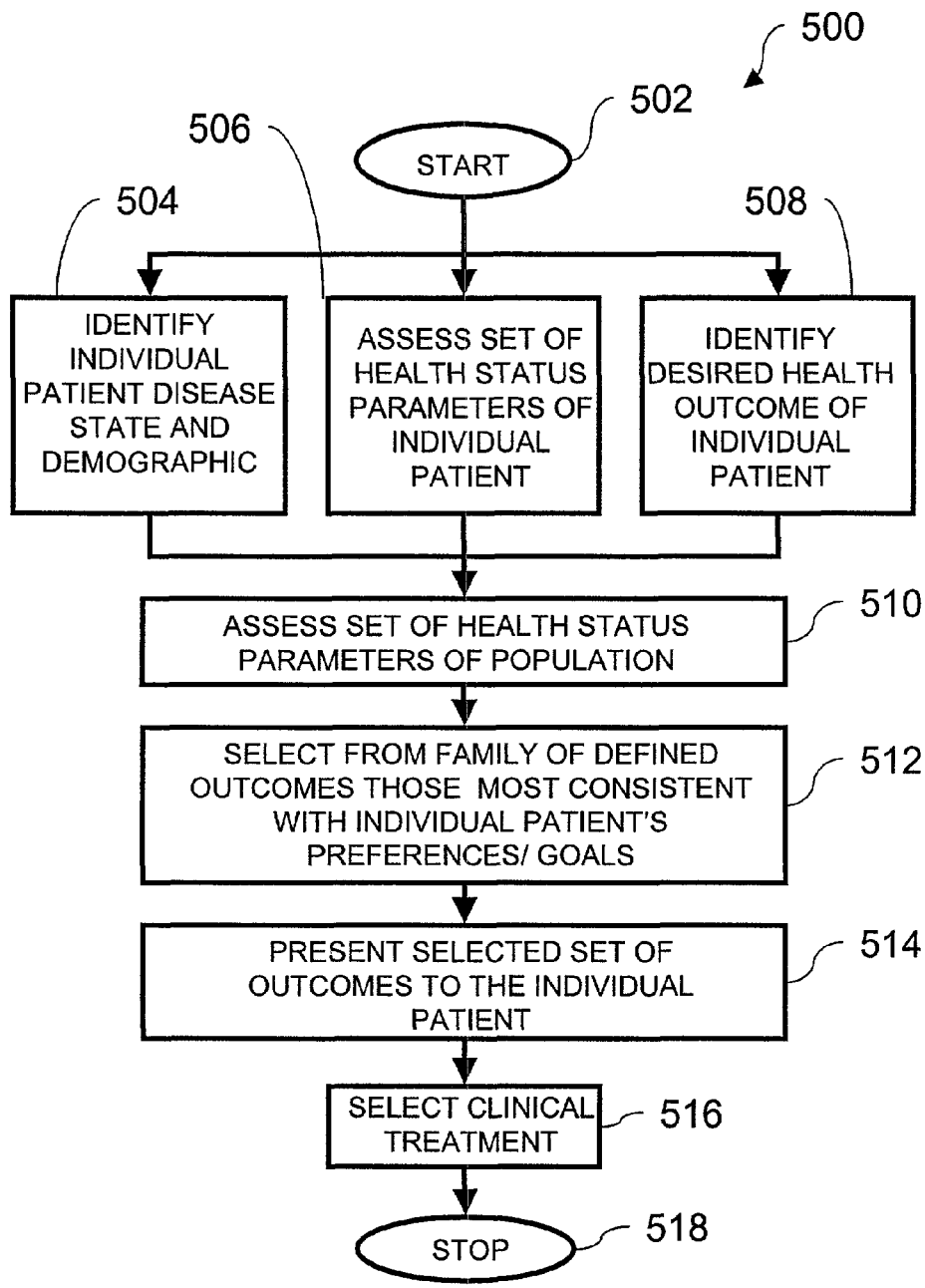
FIG. 5 is a flow diagram illustrating one method of the medical system to the present invention.

FIG. 5 shows a flow chart illustrating operation 500 of medical system 400, in accord with one method of the invention. Operation 500 commences in step 502. Processor 404 identifies a disease state and demographics of the individual patient, in step 504. Processor 404 assesses health status parameters of the individual patient, in step 506. Processor 404 identifies the projected health outcome desired by the individual patient based upon said individual preferences and goals, in step 508. Processor 404 assesses health status parameters from a population of patients having similar demographics to the individual patient to provide a library of specific projected health outcomes for each different treatment, in step 510. Processor 404 selects preferred outcomes from the library of specific projected health outcomes that similarly coincide with preferences and goals of the individual patient, in step 512. Interface 408 presents the preferred outcomes to the patient, in step 514. Processor 404 selects a clinical treatment for the patient based on the preferred outcomes, in step 516. Operation 500 ends in step 518.

Instructions that perform the operation discussed in FIG. 5 may be stored in storage media or computer memory. The instructions may be retrieved and executed by processor 404. Some examples of instructions include software, program code, and firmware. Some examples of storage media include memory devices, tapes, disks, integrated circuits, and servers. The instructions are operational when executed by processor 404 to direct processor 404 to operate in accord with the invention. Those skilled in the art are familiar with instructions and storage media.

Figure 6:
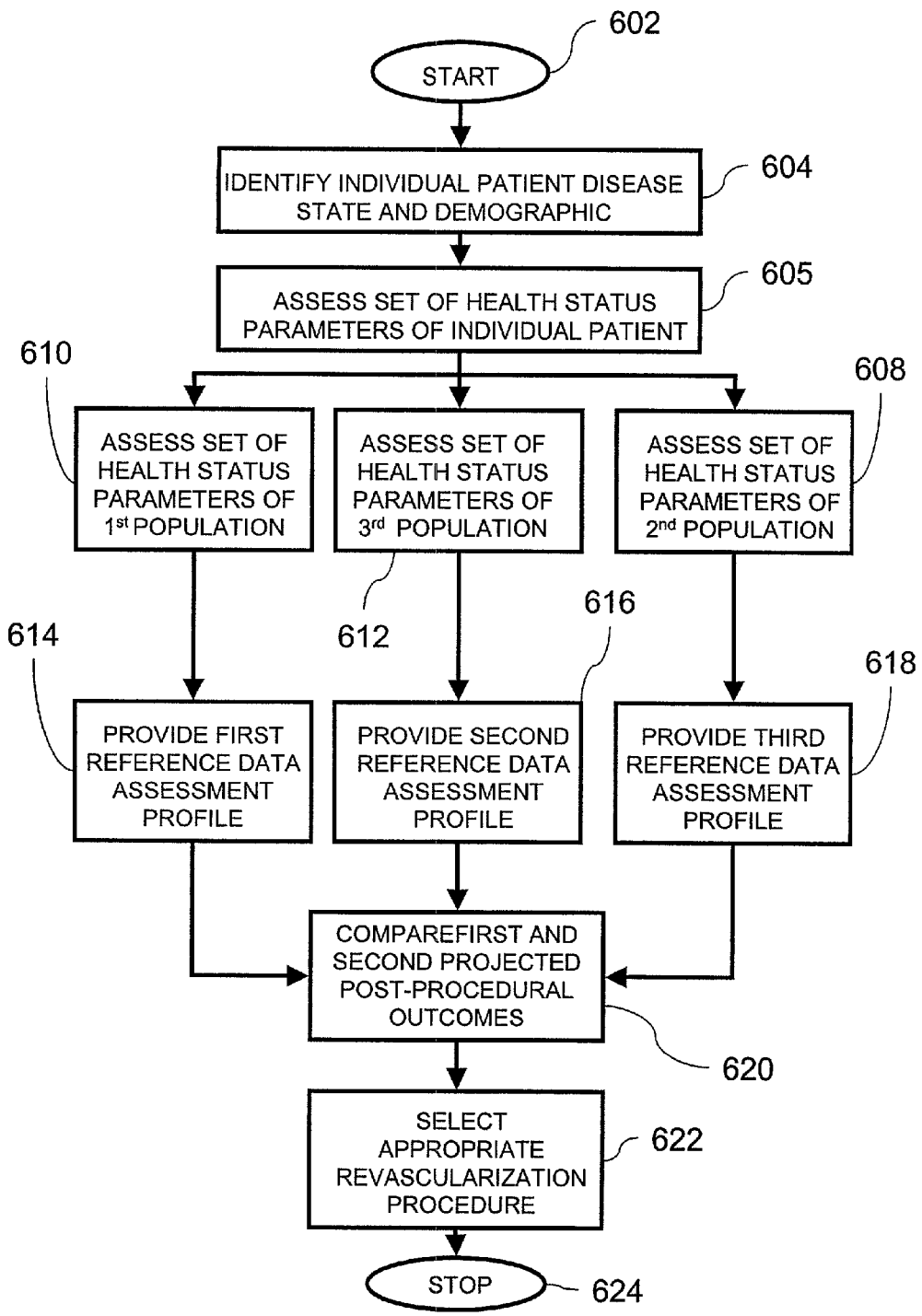
FIG. 6 is another diagram illustrating one method of the present invention.

FIG. 6 shows a flow chart illustrating operation 600 of medical system 400, in accord with one method of the invention. Operation 500 commences in step 502. Processor 404 identifies a disease state and demographics of the individual patient, in step 504. The demographics may include age, sex, economic burden, living situation, social support, employment status, type of employment, and education level of the individual patient. Processor 404 assesses set of health status parameters from the patient to provide a first data assessment profile, in step 605. Processor 404 assesses set of health status parameters from a first population of patients to provide a first reference data assessment profile, in step 610. Processor 404 assesses set of health status parameters from a second population of patients to provide a second reference data assessment profile, in step 612. Processor 404 assesses set of health status parameters from a third population of patients to provide a third reference data assessment profile, in step 608. The first, second, and third populations may have similar demographics as the individual patient and differing treatments and/or revascularization procedures. Processor 404 projects the survival and quality of life probability of the individual patient from the first, second, and third reference data assessment profiles to respectively provide first, second, and third projected post-procedural outcomes of the revascularization procedures and/or treatments, in steps 614, 616, and 618. The revascularization procedures may include a coronary artery bypass grafting (CABG) procedure and a Percutaneous Coronary Intervention (PCI) procedure. The treatment may include anti-coronary disease medication, diet modification, herbal remedy, and other non-surgical intervention procedure. Processor 404 compares the first projected post-procedural outcome to the second projected post-procedural outcome, in step 620. Processor 404 selects an appropriate revascularization procedure for the individual patient in response to the step of comparing, in step 622. Operation 600 ends in step 624.

Figure 7:
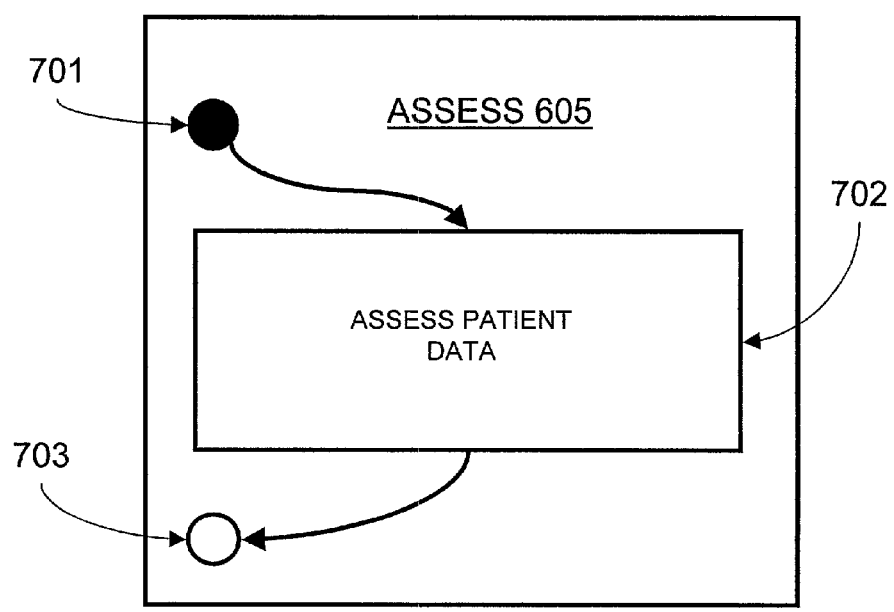
FIG. 7 is a flow diagram illustrating one step of the method of the present invention.

FIG. 7 shows a flow chart illustrating step 605 of operation 600, in accord with one method of the invention. Step 605 enters through entry point 701. Processor 404 assess the individual patient's data, in step 402. Step 605 exits through exit point 703.

Figure 8:
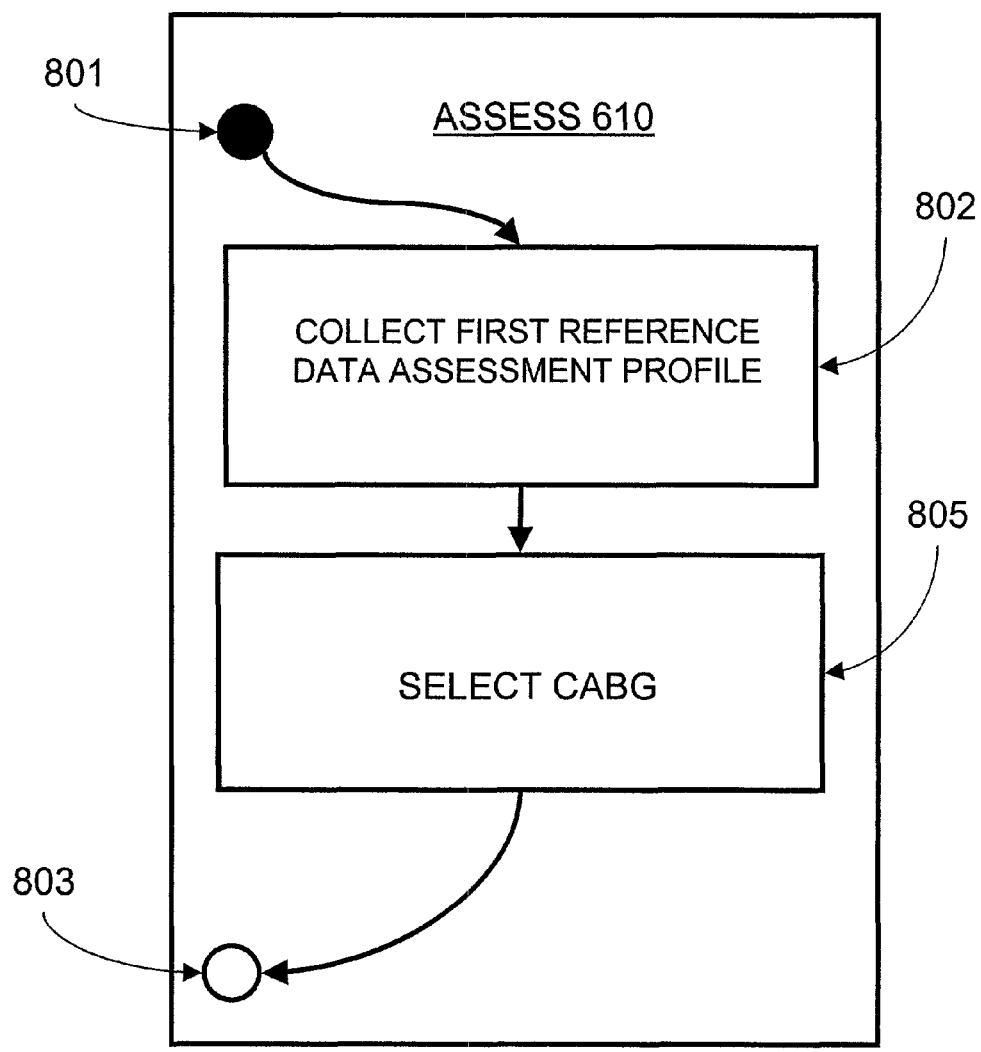
FIG. 8 is a flow diagram illustrating another step of the present invention.

FIG. 8 shows a flow chart illustrating step 610 of operation 600, in accord with one method of the invention. Step 610 enters through entry point 801. Processor 404 may collect the first data assessment profile of the first group of patients, in step 802. Processor 404 may select the CABG revascularization procedure, in step 804. Step 610 exits through exit point 803.

Figure 9:
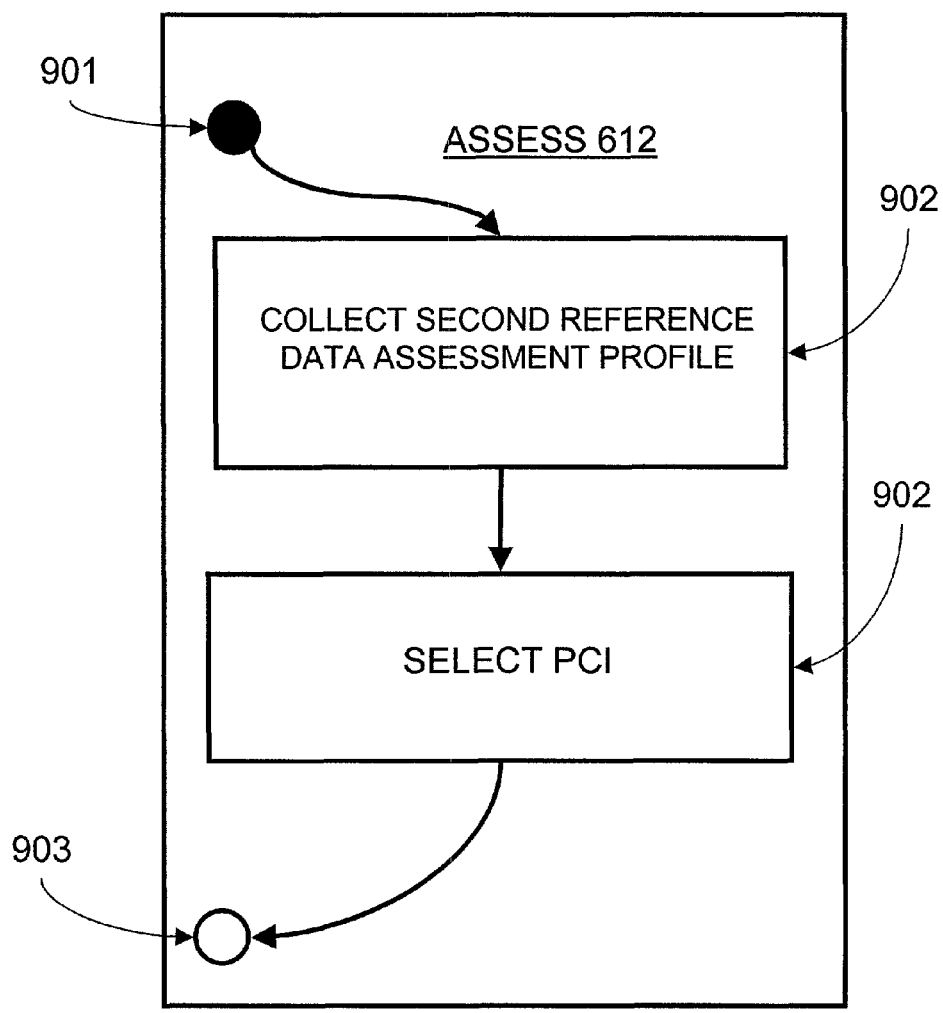
FIG. 9 is a flow diagram illustrating another step of the present invention.

FIG. 9 shows a flow chart illustrating step 612 of operation 600, in accord with one method of the invention. Step 612 enters through entry point 901. Processor 404 may collect the second data assessment profile of the second group of patients, in step 902. Processor 404 may select the PCI revascularization procedure, in step 904. Step 612 exits through exit point 903.

Figure 10:
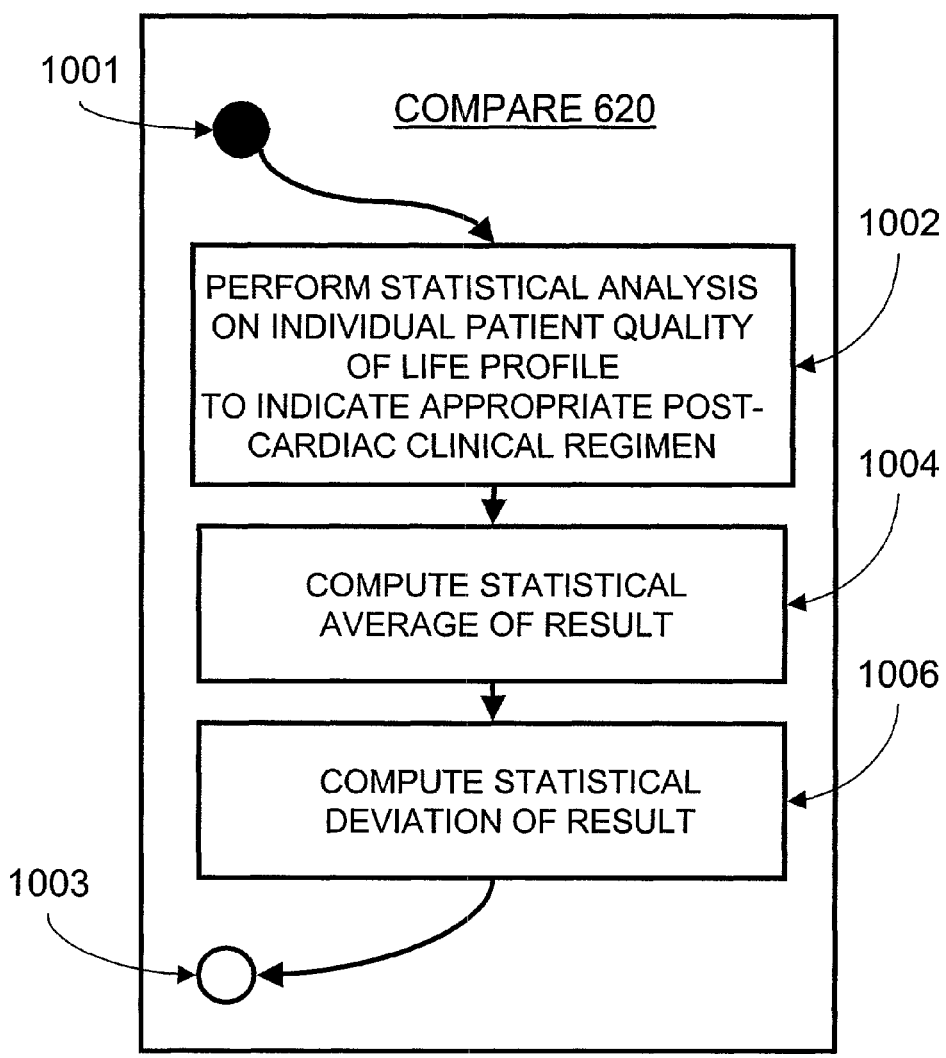
FIG. 10 is a flow diagram illustrating another step of the present invention.

FIG. 10 shows a flow chart illustrating step 620 of operation 600, in accord with one method of the invention. Step 620 enters through entry point 1001. Processor 404 may perform a statistical analysis on the individual patient quality of life profile, in step 1002. The statistical analysis may indicate to the individual patient an appropriate post-cardiac clinical regimen. Processor 404 may compute a statistical average that indicates the appropriate post-cardiac clinical regimen based on the statistical analysis, in step 1004. Processor 404 may compute a statistical deviation about the average, in step 1006. Step 620 exits through exit point 1003.

Those skilled in the art should appreciate that operation 500 and 600 are shown for illustrative purposes and that certain changes or step sequences, such as those found in steps 504, 506, and 508, may be altered as a matter of design choice.

EXAMPLE 1

The present example demonstrates the utility of the present invention for assembly and stratifying patient data as part of a tool that can be used by a patient or attending health care professional in making a choice of clinical treatment to pursue. In a general sense, the invention creates a patient outcome management system.

Using a collected, consecutive cohort of patients undergoing coronary revascularization, the critical patient and procedural characteristics that predict health status outcomes after a cardiac revascularization procedure, such as Coronary Artery Bypass Grafting (CABG) or Percutaneous Coronary Intervention (PCT), can be identified. The method of the present invention may be used in conjunction with any group of patients and collected disease-burdened population of people, such as a population of patients that suffer from arthritis, chronic obstructive pulmonary disease, cancer (brain, prostate, breast, skin, etc.), any type of peripheral vascular disease, by way of historical data may be collected and stratified according to a defined demographic profile of an individual patient considering his/her options for treatment of a disease or condition.

This demographically sorted data may then be screened to isolate those treatment regimens that resulted historically in the spectrum of health status outcomes and goals/priorities identified to be most important to the patient. From the treatment regimens that had provided at least the majority of results/consequences important to the patient, the patient may be presented with a focused set of health care treatment options to consider in making his/her decision.

By using the types of data outlined below, the patient and procedural characteristics that most influence a patients' peri-procedural and 1-year outcomes will be determined.

TABLE 1

| Patient Data | Clinical Data |
|---|---|
| Demographics | Comorbidities |
| Economic burden | Depression (MOS-D) |
| Living Situation | Rx Setting - i.e. AMI |
| Social Support | Cardiac risk factors |
| Employment | Smoking Status |
| Education | SF-12/EuroQOL |

For a patient having had a coronary disease, such as a heart attack, that is considering a revascularization procedure, the following specific data will also be tabulated and PCI (1639 patients), the present investigation identified specific post-coronary event outcomes that were identifiable with a specific selection of one revascularization event over another. The outcome data that was characteristic of the patients that were statistically analyzed for this system had been tallied one-year after the particular revascularization procedure was performed on them.

A substudy of some of these patients has been completed on 495 patients. Of these 224 patients received CABG revascularization procedure and 271 patients received a PCI revascularization procedure. All of these patients were administered baseline and monthly follow-up assessments for 6 months to model the recovery of health status after revascularization. Preliminary analysis of this substudy revealed indentifiable trends in health status outcome that were linked to the treatment protocol elected.

Previous clinical trials had reported no survival differences between PCI and CABG. Presently published results however, clearly showed that after PCI, patients are more dependent on anti-anginal mediations than CABG. Recently published clinical trial data demonstrates that 21.1% of PCI patients as compared with 41.5% of CABG patients were free of anti-anginal medications 1 year after treatment (P<0.001). Given the greater need for medications after PCI, the present investigation considers the variable that patient may have difficulty in affording their healthcare, and that these patients may have difficulty in affording their healthcare, and that these patients may have a worse health status aft PCI as compared with CABG.

EXAMPLE 2

Angina Frequency

The present example demonstrates the utility of the invention for considering health status rather than survival for managing the health care options to be presented to a patient. The present example also illustrates the utility of a new set of risk-stratification variables that are important in the medical decision variables that are important in the medical decision making process. The present example also demonstrates the utility of the present example as an efficient mechanism of collecting data about patient's current health status and of new risk-stratification variables that are useful in projecting anticipated outcomes.

The present invention further presents the inclusion of interdual patient data that is being accumulated through each new decision making event, back into the pool of data or population data that may be used/is used in a subsequent pool of patients. In this manner, the population database is constantly being updated, as well as opportunities for new treatment regimens becoming part of the decision-making process system.

The need to integrate multiple sources of data and to depict multiple types of outcomes has led to the present inventors' development of yet another aspect of the invention, a decision making tool PREDICT™, that is to be used in tailoring treatment choices to individual patients.

At the time of revascularization, the 34.3% of patients reporting an economic burden had significantly more frequent angina than those who did not (SAQ Angina Frequency score (range=0-100 where higher scores indicate less angina) =60±26 vs. 69±25 for CABG; 52±30 vs. 67±25 for PCI ($p<0.01$ for both)).

During the 6 months of follow-up, however, a persistent disparity in angina control was noted after PCI (Repeated Measures ANOVA controlling for all baseline differences between groups: $F=6.6$, $p=0.009$) but not after CABG ($F=0.06$, $p=0.8$). Similar findings were noted for SAQ physical function and quality of life domains as well. The mechanism by which economically disadvantaged patients are unable to attain the same health status after PCI as economically secure patients is unclear. The absence of such a disparity in CABG may indicate that patients who have difficulty affording medical care might preferentially select surgical revascularization.

PROPHETIC EXAMPLE 3

Identification of Determinants of Health Status

The key determinants of health status (symptoms, function, quality of life) after PCI and CABG through robust analyses of an existing database. Using the types of data described in the Table above, we will determine the key predictor variables for angina frequency, physical limitation and quality of life as measured by 12-month, post-procedure SAQ scores will be tabulated and statistically analyzed.

TABLE 2

| Procedural Data | Outcome Data |
| --- | --- |
| Number of diseased vessels | Seattle Angina Questionnaire |
| Percent Sterosis | Short Form -12 |
| Ejection Fraction | EuroQOL |
| Technique of revasc variation | Hospitalizations |
| Treatment success | Repeat procedures |
| Complications | Survival |

Data reduction will be done with clustering, stepwise variable selection and factor analysis techniques to identify the most parsimonious set of data that needs to be collected. Internal (bootstrap) validation and comparisons with external data sources will be used to validate selected variables. Given the anticipated error in predicting outcomes with any statistical model (due to unmeasured patient variability and the role of chance) the patient will not be presented with a single projected outcome for each SAQ domain. Rather, these data will be used to stratify patients and then generate the range of observed outcomes seen in similar patients treated with both PCI and CABG (see example below). This will make concrete the range of previously observed outcomes (among similar patients) and allow patients and their physicians to choose a treatment strategy that has the best trade-off between projected distributions of outcome and risk (the latter coming from the models of STS, ACC, Emory, NY State, Northern New England, etc.).

While the format and elements of outcomes projections will change, an example of the types of data that we envision presenting is shown below. In this example, a 72 year old women with diabetes, normal LV function, and difficulty affording her healthcare can see the trade-offs between the better symptom distribution, greater peri-operative risk and lower likelihood of repeat admissions and revascularization procedures of bypass surgery as compared with PCI. Such presentations of outcomes data will allow patients (and their physicians) to be more involved and, ultimately, satisfied with the process of selecting a revascularization strategy.

PROPHETIC EXAMPLE 4

Computer Program Using Observational Data Bases for Revascularization Decision Making Processes Observational databases will be used to facilitate treatment decisions for patients considering revascularization. The PREDICT™ instrument provides the vehicle that will be employed to accomplish this task. Four distinct components create PREDICT™. First, an interface for data collection is required. Second, a software program takes collected created so that collected data may be transformed into clinically meaningful distributions of projected outcomes. Third, a mechanism for customizing PREDICT™'s output so that patient-valued and readily interpretable outcomes may be displayed. And finally, the infrastructure for tracking outcomes of patients using PREDICT™ must be created so that the system can continue to grow as new treatment technologies are introduced.

PREDICT™'s networked software architecture optimization algorithms. To assist in keeping this project appraised of the most recent developments in the rapidly evolving field of software and computing design.

The first step in designing PREDICT™ is to create a mechanism for collecting the data elements identified in Example 1. The present decision tool will be seamlessly integrated into the flow of patient care. This is particularly important in the setting of coronary revascularization where the decision to perform revascularization may be made with the first injection of contrast during diagnostic angiography. The ultimate design of data collection will depend on the number and types of data needed, the current plan is to write a Palm Pilot® application for the collection of critical data elements, to identify the optimal point in patient care for their acquisition, and to synchronize collected data to a server so that we can generate the needed outcomes reports.

The second step in developing PREDICT™ is to build a software application for generating the observed outcomes distributions and predictions. Given the need to link multiple potential data sources and to incorporate these data into a series of models for output generation, a distributed network-based software system will be developed using an extensible information system (XML) to represent critical data elements. The open architecture, scalability and cross-platform utility of XML make it ideal for creating PREDICT™. Our approach will involve creating and implementing the architectural specifications for a flexible, scalable system to include data collection and representation, compute engine development, and mechanisms for generating customizable output.

The third step in creating PREDICT™ is to make the output readily interpretable. Current evidence suggests that patient's better recall and understand facts presented in numeric, probabilistic terms. In fact, the lack of access to numeric estimates has been shown to encourage patients to overestimate treatment benefits and to underestimate risk. Furthermore, the use of numeric summaries of expected outcomes improves the accuracy of physician-patient communication. In addition to the format of data, the frame of the message, in terms of health benefits (gains) or costs (losses) is also important. Research on message framing has produced mixed results with some health behaviors being influenced more by loss-oriented messages (e.g., breast self-exams,) and others by emphasizing health gains (e.g. smoking cessation). Alternative ways of framing numeric, probabilistic outcomes presentations and then conduct a series of focus groups with different data formulations (e.g., negatively vs. positively framed, different visual formats) to finalize the present approach will be developed. Insights from these exercises will provide invaluable feedback in perfecting PREDICT™'s output. Ultimately, a customizable menu of choices will be created for patients and physicians to select those outcomes that are most relevant to them. This will allow one patient, who is most concerned about returning to work, to select that outcome whereas another may choose angina relief or quality of life as the outcome that most concerns them. This will maximize the likelihood that feedback will address the goals and values of each individual patient.

The final step in creating PREDICT™ is to build an infrastructure for follow-up. As patient data is entered into PREDICT™, it can provide the baseline assessment for following that individual's outcome over time. For this reason, we will design PREDICT™'s software to allow maximal use of all collected data. Once accomplished, collected baseline data will be synchronized with procedural and follow-up databases so that 1 year after initial treatment, patients can be contacted for follow-up. As follow-up data is captured, those patients' data will enter the repository from which future patients will see the distribution of outcomes associated with patients who were similar to them. This creates a continuously evolving system that minimizes the delay in updating outcomes projections in an era of rapid technological change.

PROPHETIC EXAMPLE 5

Pilot Test of PREDICT™

Throughout the process of developing PREDICT™, ongoing feedback from patients and physicians will be acquired through individual interviews and focus groups. Ultimately, however, an explicit demonstration of its feasibility will be needed. The final goal of this proposal will be to conduct a 1-month pilot test. The complete design of such testing cannot be definitively described because the precise parameters that will dictate usage will evolve from the steps outlined in Specific Aims 1 and 2. Conceptually, however, we plan to adopt the following basic approach: PREDICT™ will be implemented among a consecutive cohort of patients and describe the time required for implementation, the percent of patients eligible in whom the tool was used, the physicians' assessment whether the tool provides value to outweigh the time required in its use and patients' satisfaction with decision making as assessed by the Satisfaction with Decision scale[9]. Once the insights from this pilot study are reviewed and analyzed, a multicenter trial of PREDICT™ will be created to assess its impact on patient choices for revascularization, satisfaction, cost and outcome.

I claim:

1. A non-transitory computer readable storage medium storing instructions that when executed by a computer system, cause the computer system to perform operations comprising:
   accessing a database to retrieve information regarding a first individual patient;
   identifying a disease state of the first individual patient using information accessed from the database;
   assessing health status parameters of the first individual patient;
   identifying a projected health outcome corresponding to the first individual patient based upon a preference of the first individual patient and on a goal of the first individual patient;
   accessing the database to retrieve information regarding health status parameters from a population having similar demographics to the first individual patient to provide a library of projected health outcomes for a plurality of treatments for the disease state of the first individual patient; and
   at least partly based on the first individual patient's goal and preference, assisting the patient and or provider in selecting preferred outcomes from the library of projected health outcomes.

2. The non-transitory computer readable storage medium as defined in claim 1, wherein the operations further comprise:
   assessing health status parameters from a first population of patients selected from the population having similar demographics to the first individual patient to provide a first reference data assessment profile;
   assessing health status parameters from a second population of patients selected from the population having similar demographics to the first individual patient to provide a second reference data assessment profile;
   assessing health status parameters from a third population of patients selected from the population having similar demographics to the first individual patient to provide a third reference data assessment profile;
   wherein the first, second, and third populations have had correspondingly different treatments for the disease state,
   wherein the survival and quality of life probability of the first individual patient is projected from the first, second, and third reference data assessment profiles to respectively provide first, second and third projected post-procedural outcomes, and
   wherein at least the first and second post-procedural outcomes are compared to select an appropriate procedure for the first individual patient.

3. The non-transitory computer readable storage medium as defined in claim 1, wherein the operations further comprise: predicting health status outcomes for the first individual patient with respect to a cardiac revascularization procedure performed on the first individual patient.

4. The non-transitory computer readable storage medium as defined in claim 1, wherein the operations further comprise: indicating an appropriate post-cardiac clinical regime using a statistical analysis on a quality of life profile associated with the first individual patient.

5. The non-transitory computer readable storage medium as defined in claim 1, wherein the operations further comprise indicating an appropriate post-cardiac clinical regime by performing a statistical analysis on the first individual patient's quality of life profile, compute a statistical average based on the statistical analysis, and compute a statistical deviation about the average.

6. The non-transitory computer readable storage medium as defined in claim 1, wherein the operations further comprise:
   predicting health status outcomes for at least one individual patient suffering from one or more of the following conditions: arthritis, chronic obstructive pulmonary disease, cancer, and/or a peripheral vascular, disease,
   by isolating treatment regimens for the one or more conditions that resulted historically in health status outcomes and goals corresponding to those of the first individual patient to thereby provide the first individual patient with a corresponding set of health care options from which to select.

7. The non-transitory computer readable storage medium as defined in claim 1, wherein the first individual patient's health status is determined based on the first individual patient's symptoms, function, and quality of life.

8. The non-transitory computer readable storage medium as defined in claim 1, wherein the first individual patient's demographics include economic burden, and
   the preferred outcomes are selected by the computer system based at least in part on the first individual patient's economic burden.

9. The non-transitory computer readable storage medium as defined in claim 1, wherein the first individual patient's demographics include living situation, and
   the preferred outcomes are selected by the computer system based at least in part on the first individual patient's living situation.

10. The non-transitory computer readable storage medium as defined in claim 1, wherein the first individual patient's demographics include social support and,
    the preferred outcomes are selected by the computer system based at least in part on the first individual patient's social support.

11. The non-transitory computer readable storage medium as defined in claim 1, wherein the first individual patient's demographics include employment status, and
    the preferred outcomes are selected by the computer system based at least in part on the first individual patient's employment status.

12. The non-transitory computer readable storage medium as defined in claim 1, wherein the first individual patient's demographics include type of employment, and
    the preferred outcomes are selected by the computer system based at least in part on the first individual patient's type of employment.

13. The non-transitory computer readable storage medium as defined in claim 1, wherein the first individual patient's demographics include education level, and
    the preferred outcomes are selected by the computer system based at least in part on the first individual patient's education level.

14. The non-transitory computer readable storage medium as defined in claim 1, wherein the first individual patient's disease state includes clinical data relating to comorbidities, and
    the preferred outcomes are selected by the computer system based at least in part on the first individual patient's clinical data relating to comorbidities.

15. The non-transitory computer readable storage medium as defined in claim 1, wherein the first individual patient's disease state includes clinical data relating to depression and,
    the preferred outcomes are selected by the computer system based at least in part on the first individual patient's clinical data relating to depression.

16. The non-transitory computer readable storage medium as defined in claim 1, wherein the first individual patient's disease state includes clinical data relating to a medicine setting, and
    the preferred outcomes are selected by the computer system based at least in part on the first individual patient's clinical data relating to the medicine setting.

17. The non-transitory computer readable storage medium as defined in claim 1, wherein the first individual patient's disease state includes clinical data relating to cardiac risk factors, and
    the preferred outcomes are selected by the computer system based at least in part on the first individual patient's clinical data relating to the cardiac risk factors.

18. The non-transitory computer readable storage medium as defined in claim 1, wherein the first individual patient's disease state includes clinical data relating to smoking status, and
    the preferred outcomes are selected by the computer system based at least in part on the first individual patient's clinical data relating to the smoking status.

19. The non-transitory computer readable storage medium as defined in claim 1, wherein the information regarding health status parameters from the population having similar demographics to the first individual patient includes responses to a standardized questionnaire having a plurality of questions regarding demographic and clinical information from a plurality of patients.

20. The non-transitory computer readable storage medium as defined in claim 1, wherein the standardized questionnaire includes the Seattle Angina Questionnaire.

* * * * *

UNITED STATES PATENT AND TRADEMARK OFFICE
CERTIFICATE OF CORRECTION

PATENT NO.       : 8,744,867 B2
APPLICATION NO.  : 10/165855
DATED            : June 3, 2014
INVENTOR(S)      : John Albert Spertus It is certified that error appears in the above-identified patent and that said Letters Patent is hereby corrected as shown below:

On the Title Page

In column 2 (page 1, item 56) at line 10, Under Other Publications, change "Oregon.*" to --Oregon].*--.

Page 1 (item 57, Abstract) at line 14, Change "speiocifically" to --specifically--.

In column 2 (page 2, item 56) at line 6, Under Other Publications, change "Rish" to --Risk--.

In column 2 (page 2, item 56) at line 44, Under Other Publications, change "medcacl" to --medcalc--.

In column 2 (page 2, item 56) at line 49, Under Other Publications, change "Depolyment" to --Deployment--.

In the Drawings

Figure 1A:
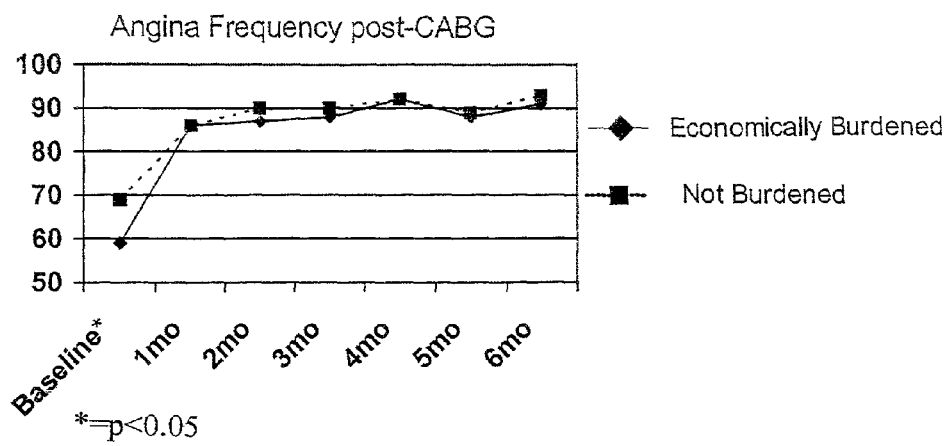
FIGS. 1A and 1B.
Figure 1B:
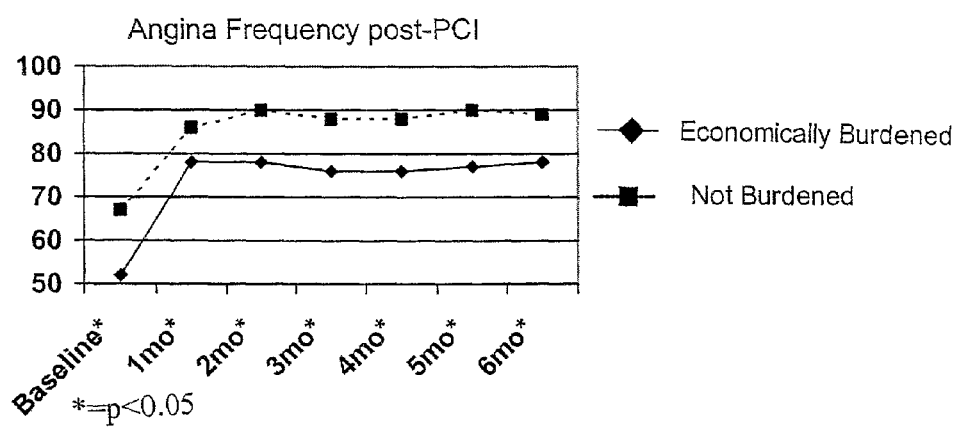
Figure 2:
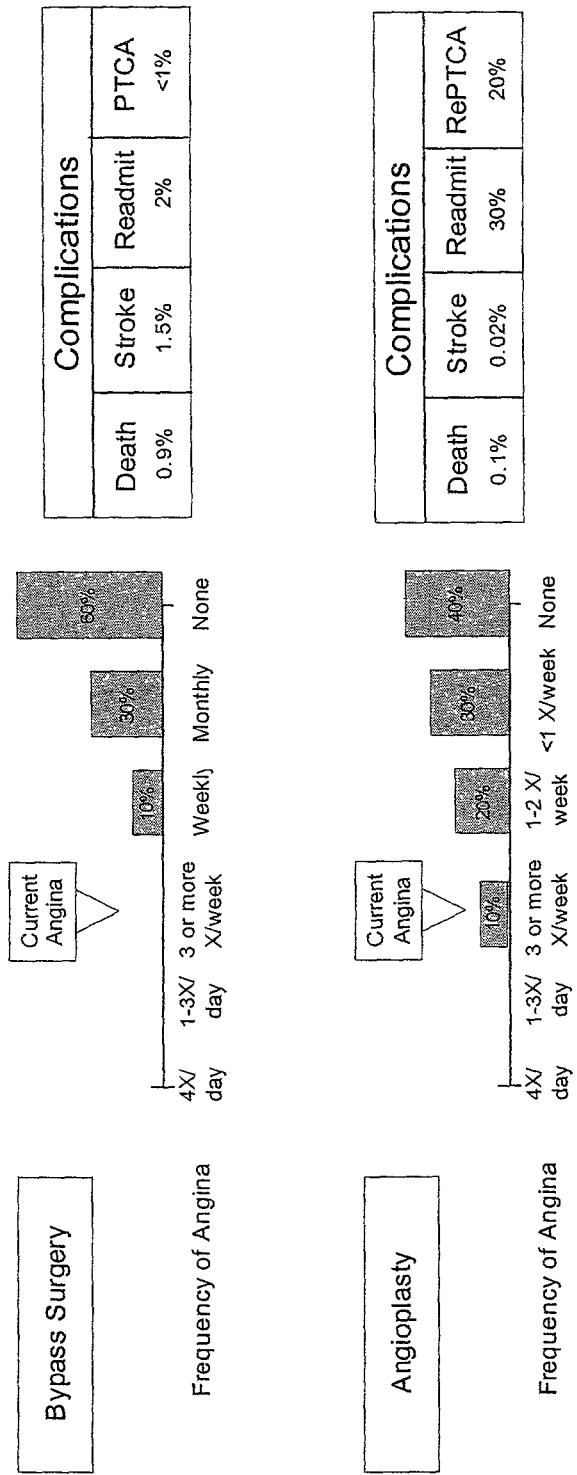
FIGS. 2A and 2B—FIG. 2A is a graph demonstrating the frequency of angina in a post-coronary attack patient having had bypass surgery. The complications monitored in these patients were death (0.9%), stroke (1.5%), readmit (2%) and PTCA (less than 1%).

Sheet 2 of 10 (FIG. 2) at line 6 (approx.), Change " Weekl) " to -- Weekly --.

Sheet 6 of 10 (Ref. Numeral 620, FIG. 6) at line 1, Change "COMPAREFIRST" to --COMPARE FIRST--.

In the Specification

In column 1 at line 24, Change "as been used as" to --as--.

In column 1 at line 48, Change "decision" to --decision.--.

In column 1 at line 53, Change "revasularization" to --revascularization--.

In column 1 at line 55, Change "treament" to --treatment--.

In column 2 at line 5, Change "des" to --does--.

In column 2 at line 40, Change "econonmically" to --economically--.

Signed and Sealed this
Ninth Day of December, 2014

Michelle K. Lee
*Deputy Director of the United States Patent and Trademark Office*

CERTIFICATE OF CORRECTION (continued)
U.S. Pat. No. 8,744,867 B2

In column 6 at line 40, Change "indentifiable" to --identifiable--.

In column 6 at line 45, Change "mediations" to --medications--.

In column 7 (TABLE 2) at line 3, Change "Sterosis" to --Stenosis--.

In the Claims

In column 10 at line 26, In Claim 1, change "and or" to --and/or--.

In column 11 at line 11, In Claim 6, change "vascular, disease," to --vascular disease,--.